United States Patent [19]
Berthon-Jones

[11] Patent Number: 6,123,082
[45] Date of Patent: Sep. 26, 2000

[54] DEVICE FOR PREVENTING OR REDUCING THE PASSAGE OF AIR THROUGH THE MOUTH

[75] Inventor: Michael Berthon-Jones, Leonay, Australia

[73] Assignee: ResMed Limited, North Ryde, Australia

[21] Appl. No.: 08/943,259

[22] Filed: Oct. 3, 1997

[30] Foreign Application Priority Data

Dec. 18, 1996 [AU] Australia .................................. PO4256

[51] Int. Cl.⁷ ...................................................... A61B 19/00
[52] U.S. Cl. ........................ 128/863; 128/857; 128/859; 128/207.15; D29/108
[58] Field of Search ..................................... 128/846, 848, 128/857, 859, 863, 201.18, 201.22, 206.21, 206.24, 206.27, 207.15, 207.17, 860, 861, 862; D24/191; D29/108; 606/157; 2/9, 206, 424, 909, 919

[56] References Cited

U.S. PATENT DOCUMENTS

| D. 32,565 | 4/1900 | Hooper .................................... D29/108 |
|---|---|---|
| Re. 35,339 | 10/1996 | Rapoport . |
| D. 293,613 | 1/1988 | Wingler . |
| D. 293,840 | 1/1988 | Parrish ..................................... D29/17 |
| 306,946 | 10/1884 | Olsen . |
| D. 323,908 | 2/1992 | Hollister et al. . |
| D. 334,633 | 4/1993 | Rudolph . |
| D. 380,871 | 7/1997 | Guyette, Jr. ............................. D29/108 |
| 390,027 | 9/1888 | Locke .................................. 128/206.12 |
| 712,304 | 10/1902 | Jacobs et al. ....................... 128/206.12 |

(List continued on next page.)

FOREIGN PATENT DOCUMENTS

| 91/77110 | 11/1991 | Australia . |
|---|---|---|
| 94/64816 | 12/1994 | Australia . |
| B 79174/94 | 6/1995 | Australia . |
| 95/16178 | 7/1995 | Australia . |
| 89312/98 | 1/1999 | Australia . |
| 0 062 166 A2 | 10/1982 | European Pat. Off. . |
| 0 185 980 | 7/1986 | European Pat. Off. . |
| 0 872 643 A2 | 3/1988 | European Pat. Off. . |
| 0 388 525 A1 | 9/1990 | European Pat. Off. . |
| 0427474 A2 | 5/1991 | European Pat. Off. . |
| 0 481 459 A1 | 4/1992 | European Pat. Off. . |
| 0549299 A2 | 6/1993 | European Pat. Off. . |
| 0705615 A1 | 9/1994 | European Pat. Off. . |

(List continued on next page.)

OTHER PUBLICATIONS

Mask 1 Photographs, Respironics Inc., Reusable Full Mask (small) Part #452033 Lot # 951108.
Mask 2 Photographs, Puritan—Bennett, Adam Curcuit, Shell Part # 231700, Swivel Part # 616329–00, Pillows (medium) Part #616324.
Mask 3, Photographs, DeVilbiss Healthcare Inc., DeVilbiss Seal–Ring and CPAP Mask Kit (medium), Part 73510–669.
Mask 4 Photographs, Respironics Inc., Monarch Mini Mask with Pressure Port. Part # 572004, Monarch Headgear, Part # 572011.
Mask 5 Photographs, Healthdyne Technologies, Nasal CPAP Mask (medium narrow), Part # 702510.
Mask 6 Photographs, Healthdyne Technologies, Soft Series Nasal CPAP Mask, Part # 702020.
Mask 7 Photographs, DeVilbiss Healthcare Inc., Small Mask and Seal Rings, Part # 73510–668.

(List continued on next page.)

Primary Examiner—John G. Weiss
Assistant Examiner—Joseph F. Weiss, Jr.
Attorney, Agent, or Firm—Pillsbury Madison & Sutro LLP

[57] ABSTRACT

A device (20) for preventing or reducing the passage of air through the mouth (22). The device (20) comprises a top lip member (26) and a bottom lip member (28) having a space (34) therebetween. The space (34) is configured such that, in use, when the top and bottom lips (22T & 22B) of a patient are forced through the space (34), the top and bottom lip members (26 & 28) squeeze the top and bottom lips (22T & 22B) together thereby substantially sealing the mouth (22).

29 Claims, 9 Drawing Sheets

U.S. PATENT DOCUMENTS

| | | | |
|---|---|---|---|
| 737,591 | 9/1903 | Dempsey | 128/206.12 |
| 781,516 | 1/1905 | Guthrie . | |
| 812,706 | 2/1906 | Warbasse . | |
| 1,081,745 | 12/1913 | Johnston et al. . | |
| 1,171,973 | 2/1916 | Patterson | 128/848 |
| 1,192,186 | 7/1916 | Greene . | |
| 1,354,652 | 10/1920 | Jefferies | 128/848 |
| 1,492,387 | 4/1924 | Pool | 128/848 |
| 1,635,272 | 7/1927 | Hartl | 128/848 |
| 1,653,572 | 12/1927 | Jackson . | |
| 1,775,718 | 9/1930 | Garvey | 128/846 |
| 1,926,027 | 9/1933 | Biggs . | |
| 2,098,340 | 11/1937 | Henahan | 128/848 |
| 2,248,477 | 7/1941 | Lombard . | |
| 2,317,608 | 9/1943 | Heidbrink . | |
| 2,371,965 | 3/1945 | Lehmberg . | |
| 2,376,871 | 5/1945 | Fink . | |
| 2,415,846 | 2/1947 | Randall . | |
| 2,438,058 | 3/1948 | Kincheloe . | |
| 2,578,621 | 12/1951 | Yant . | |
| 3,013,556 | 12/1961 | Galleher . | |
| 3,099,985 | 8/1963 | Wilson et al. . | |
| 3,182,659 | 5/1965 | Blount et al. . | |
| 3,189,027 | 6/1965 | Bartlett . | |
| 3,193,624 | 7/1965 | Webb et al. . | |
| 3,238,943 | 3/1966 | Holley . | |
| 3,362,420 | 1/1968 | Blackburn et al. . | |
| 3,363,833 | 1/1968 | Laerdal . | |
| 3,502,100 | 3/1970 | Jonson . | |
| 3,556,122 | 1/1971 | Laerdal . | |
| 3,700,000 | 10/1972 | Hesse et al. . | |
| 3,720,235 | 3/1973 | Schrock . | |
| 3,726,270 | 4/1973 | Griffis et al. . | |
| 3,741,208 | 6/1973 | Jonsson et al. . | |
| 3,796,216 | 3/1974 | Schwarz . | |
| 3,799,164 | 3/1974 | Rollins . | |
| 3,914,994 | 10/1975 | Banner . | |
| 3,995,661 | 12/1976 | Van Fossen . | |
| 4,077,404 | 3/1978 | Elam . | |
| 4,109,749 | 8/1978 | Sweet . | |
| 4,119,096 | 10/1978 | Drews . | |
| 4,206,754 | 6/1980 | Cox et al. . | |
| 4,226,234 | 10/1980 | Gunderson . | |
| 4,245,632 | 1/1981 | Houston . | |
| 4,249,527 | 2/1981 | Ko et al. . | |
| 4,304,229 | 12/1981 | Curtin . | |
| 4,312,235 | 1/1982 | Daigle . | |
| 4,328,797 | 5/1982 | Rollins, III et al. . | |
| 4,347,205 | 8/1982 | Stewart . | |
| 4,396,034 | 8/1983 | Cherniak . | |
| 4,412,537 | 11/1983 | Tiger . | |
| 4,449,525 | 5/1984 | White et al. . | |
| 4,481,944 | 11/1984 | Bunnell . | |
| 4,519,399 | 5/1985 | Hori . | |
| 4,522,639 | 6/1985 | Ansite et al. . | |
| 4,543,950 | 10/1985 | Keys, Jr. | 128/203.26 |
| 4,558,710 | 12/1985 | Eichler . | |
| 4,579,114 | 4/1986 | Gray et al. . | |
| 4,592,880 | 6/1986 | Murakami . | |
| 4,616,647 | 10/1986 | McCreadie . | |
| 4,622,964 | 11/1986 | Flynn . | |
| 4,671,271 | 6/1987 | Bishop et al. . | |
| 4,677,975 | 7/1987 | Edgar et al. . | |
| 4,739,755 | 4/1988 | White et al. . | |
| 4,747,403 | 5/1988 | Gluck et al. . | |
| 4,773,411 | 9/1988 | Downs . | |
| 4,774,941 | 10/1988 | Cook . | |
| 4,799,477 | 1/1989 | Lewis . | |
| 4,802,485 | 2/1989 | Bowers et al. . | |
| 4,819,629 | 4/1989 | Jonson . | |
| 4,821,713 | 4/1989 | Bauman . | |
| 4,825,881 | 5/1989 | Bessler | 128/859 |
| 4,841,953 | 6/1989 | Dodrill . | |
| 4,848,366 | 7/1989 | Aita et al. . | |
| 4,856,506 | 8/1989 | Jinotti . | |
| 4,870,963 | 10/1989 | Carter . | |
| 4,883,072 | 11/1989 | Bessler | 128/857 |
| 4,910,806 | 3/1990 | Baker et al. . | |
| 4,919,128 | 4/1990 | Kopala et al. . | |
| 4,928,684 | 5/1990 | Breitenfelder et al. . | |
| 4,938,210 | 7/1990 | Shene . | |
| 4,938,212 | 7/1990 | Gnook et al. . | |
| 4,944,310 | 7/1990 | Sullivan . | |
| 4,957,107 | 9/1990 | Sipin . | |
| 4,986,269 | 1/1991 | Hakkinen . | |
| 4,989,596 | 2/1991 | Macis et al. . | |
| 4,989,599 | 2/1991 | Carter . | |
| 5,005,568 | 4/1991 | Loescher et al. . | |
| 5,042,473 | 8/1991 | Lewis . | |
| 5,042,478 | 8/1991 | Kopala et al. . | |
| 5,046,200 | 9/1991 | Feder . | |
| 5,046,491 | 9/1991 | Derrick . | |
| 5,048,515 | 9/1991 | Sanso . | |
| 5,063,922 | 11/1991 | Hakkinen . | |
| 5,063,938 | 11/1991 | Beck et al. . | |
| 5,099,837 | 3/1992 | Russel, Sr. et al. . | |
| 5,107,830 | 4/1992 | Younes . | |
| 5,107,831 | 4/1992 | Halpern et al. . | |
| 5,109,839 | 5/1992 | Blasdell et al. . | |
| 5,109,840 | 5/1992 | Daleiden . | |
| 5,127,411 | 7/1992 | Schoolman et al. | 128/863 |
| 5,129,390 | 7/1992 | Chopin et al. . | |
| 5,133,347 | 7/1992 | Huennebeck . | |
| 5,140,980 | 8/1992 | Haughey et al. . | |
| 5,140,982 | 8/1992 | Bauman . | |
| 5,148,802 | 9/1992 | Sanders et al. . | |
| 5,159,938 | 11/1992 | Laughlin . | |
| 5,165,398 | 11/1992 | Bird . | |
| 5,178,138 | 1/1993 | Walstrom et al. . | |
| 5,203,343 | 4/1993 | Axe et al. . | |
| 5,230,330 | 7/1993 | Price . | |
| 5,231,983 | 8/1993 | Matson et al. . | |
| 5,233,978 | 8/1993 | Callaway . | |
| 5,239,994 | 8/1993 | Atkins . | |
| 5,239,995 | 8/1993 | Estes et al. . | |
| 5,245,995 | 9/1993 | Sullivan et al. . | |
| 5,265,595 | 11/1993 | Rudolph . | |
| 5,279,289 | 1/1994 | Kirk . | |
| 5,280,784 | 1/1994 | Kohler . | |
| 5,303,698 | 4/1994 | Tobia et al. . | |
| 5,303,700 | 4/1994 | Weismann et al. . | |
| 5,311,862 | 5/1994 | Blasdell et al. . | |
| 5,311,875 | 5/1994 | Stasz . | |
| 5,322,057 | 6/1994 | Raabe et al. . | |
| 5,335,656 | 8/1994 | Bowe et al. . | |
| 5,357,951 | 10/1994 | Ratner . | |
| 5,372,130 | 12/1994 | Stern et al. . | |
| 5,373,842 | 12/1994 | Olsson et al. . | |
| 5,388,571 | 2/1995 | Roberts et al. . | |
| 5,398,673 | 3/1995 | Lambert . | |
| 5,400,777 | 3/1995 | Olsson et al. . | |
| 5,404,871 | 4/1995 | Goodman et al. . | |
| 5,419,318 | 5/1995 | Tayebi . | |
| 5,431,158 | 7/1995 | Tirotta . | |
| 5,443,061 | 8/1995 | Champain et al. . | |
| 5,458,137 | 10/1995 | Axe et al. . | |
| 5,479,920 | 1/1996 | Piper et al. . | |
| 5,488,948 | 2/1996 | Dubruille et al. . | |
| 5,509,404 | 4/1996 | Lloyd et al. . | |
| 5,509,414 | 4/1996 | Hok . | |
| 5,526,805 | 6/1996 | Lutz et al. . | |
| 5,535,739 | 7/1996 | Rapoport et al. . | |

| | | |
|---|---|---|
| 5,538,000 | 7/1996 | Rudolph . |
| 5,546,933 | 8/1996 | Rapoport et al. . |
| 5,546,936 | 8/1996 | Virag et al. . |
| 5,560,354 | 10/1996 | Berthon-Jones et al. . |
| 5,567,127 | 10/1996 | Wentz . |
| 5,608,647 | 3/1997 | Rubsamen et al. . |
| 5,617,846 | 4/1997 | Graetz et al. . |
| 5,633,552 | 5/1997 | Lee et al. . |
| 5,642,730 | 7/1997 | Baran . |
| 5,645,053 | 7/1997 | Remmers et al. . |
| 5,649,532 | 7/1997 | Oren . |
| 5,649,533 | 7/1997 | Griffiths . |
| 5,655,520 | 8/1997 | Howe et al. . |
| 5,657,493 | 8/1997 | Ferrero et al. . |
| 5,660,174 | 8/1997 | Jacobelli .............................. 128/206.24 |
| 5,662,101 | 9/1997 | Ogden et al. . |
| 5,682,878 | 11/1997 | Ogden . |
| 5,685,296 | 11/1997 | Zdrojkowski et al. . |
| 5,687,715 | 11/1997 | Landis et al. . |
| 5,704,345 | 1/1998 | Berthon-Jones . |
| 5,715,812 | 2/1998 | Deighan et al. . |
| 5,715,814 | 2/1998 | Ebers . |
| 5,794,615 | 8/1998 | Estes . |
| 5,813,423 | 9/1998 | Kirchgeorg . |
| 5,823,187 | 10/1998 | Estes et al. . |
| 5,832,918 | 11/1998 | Pantino . |

FOREIGN PATENT DOCUMENTS

| | | |
|---|---|---|
| 2574657 | 6/1986 | France . |
| 159396 | 6/1981 | German Dem. Rep. . |
| 459104 | 4/1928 | Germany .............................. 128/848 |
| 593217 | 2/1934 | Germany .............................. 128/857 |
| 34 02 603 A1 | 8/1985 | Germany . |
| 3539073 | 5/1987 | Germany . |
| 4343205 A1 | 6/1995 | Germany . |
| 4432219 C1 | 4/1996 | Germany . |
| 298 10 846 U1 | 8/1998 | Germany . |
| 605648 | 1/1960 | Italy ....................................... 128/848 |
| 60-212607 | 10/1985 | Japan . |
| 2-173397 | 12/1988 | Japan . |
| 4-70516 | 3/1992 | Japan . |
| 9/216240A | 8/1997 | Japan . |
| 1710064 A1 | 2/1992 | Sweden . |
| 2473 | of 1893 | United Kingdom .............. 128/204.13 |
| 2145335 | 3/1985 | United Kingdom . |
| 2 271 811 | 4/1994 | United Kingdom . |
| WO 82/03548 | 10/1982 | WIPO . |
| WO 93/08857 | 5/1993 | WIPO . |
| WO 93/09834 | 5/1993 | WIPO . |
| WO 93/21982 | 11/1993 | WIPO . |
| WO 94/02190 | 2/1994 | WIPO . |
| WO 94/20051 | 9/1994 | WIPO . |
| WO 97/28838 | 8/1997 | WIPO . |
| WO 97/41812 | 11/1997 | WIPO . |
| WO 97/41911 | 11/1997 | WIPO . |
| WO 98/35715 | 8/1998 | WIPO . |
| WO 98/36245 | 8/1998 | WIPO . |
| WO 98/36338 | 8/1998 | WIPO . |
| WO 98/47554 | 10/1998 | WIPO . |
| WO 98/48878 | 11/1998 | WIPO . |
| WO 98/57691 | 12/1998 | WIPO . |

OTHER PUBLICATIONS

Mask 8 Photographs, Respironics Inc., Reusable Contour Mask (medium), Part # 302180.

Mask 9 Photographs, Healthdyne Technologies, Healthdyne Large Headgear.

Mask 10 Photographs, Respironics Inc., Soft Cap (medium), Part # 302142.

Mask 11 Photographs, Weinmann: Hamburg, Nasalmaskensystem mit Schalldämpfer (medium), Part # WN 23105.

Mask 12 Photographs, Life Care.

Mask 13 Photographs, Healthdyne Technologies.

Mask 14 Photograph, King System.

Mask 15 Photographs, Respironics Inc., Paediatric Mask.

Mask 16 Photographs, Hans Rudolph Inc., Hans Rudolph Silicone Rubber Face Mask/8900.

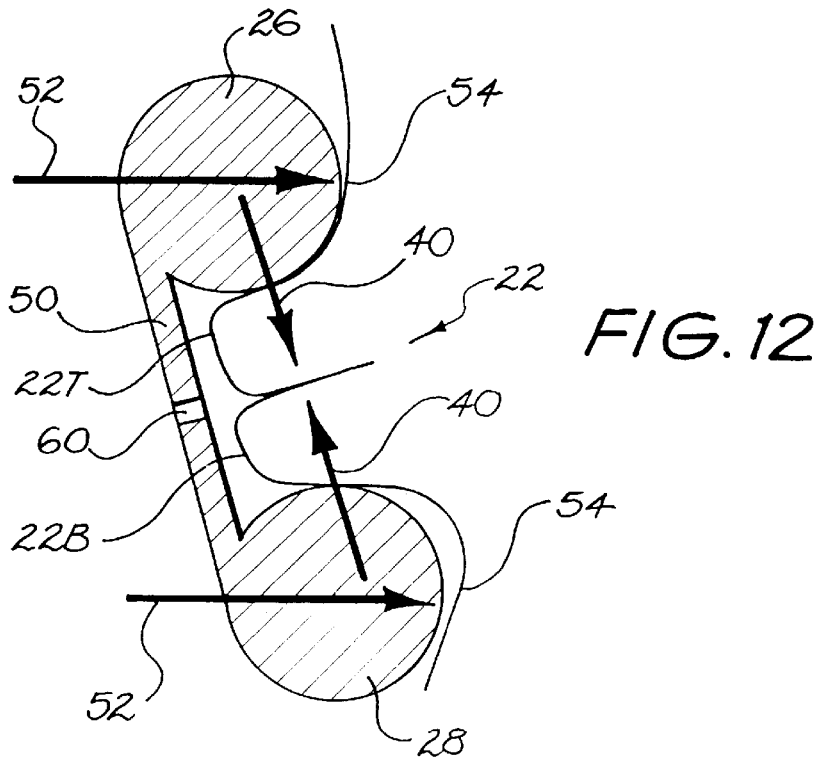
FIG. 12
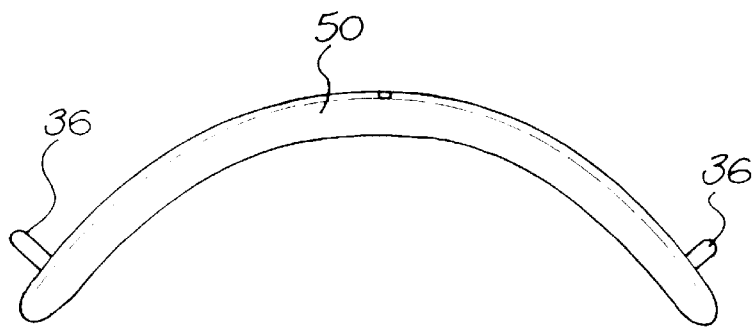
FIG. 13
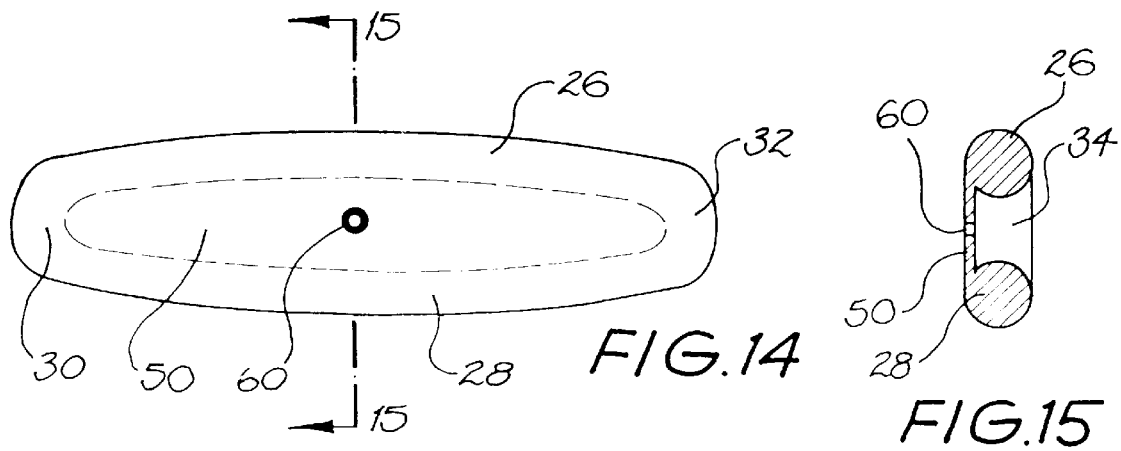
FIG. 14
FIG. 15

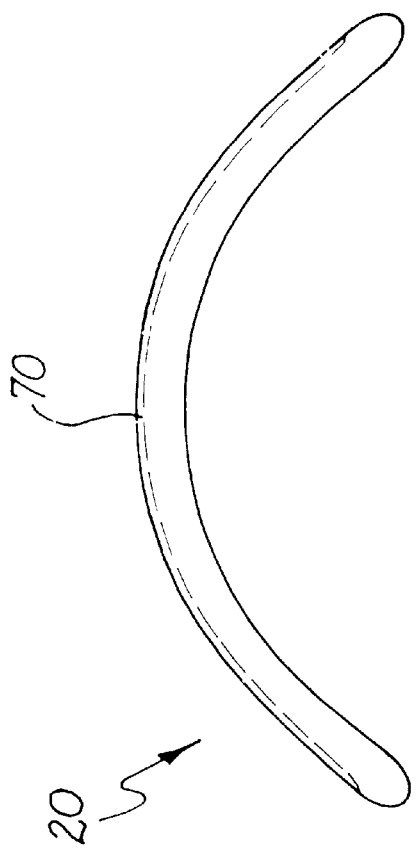
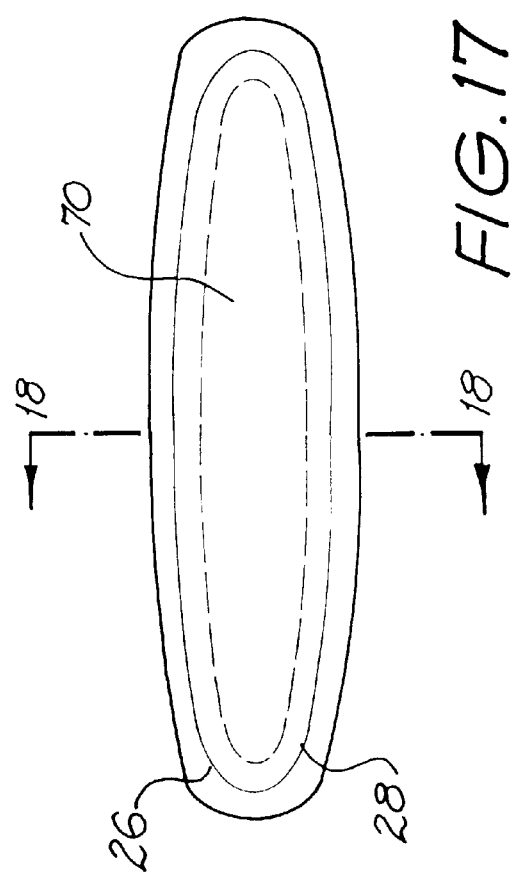
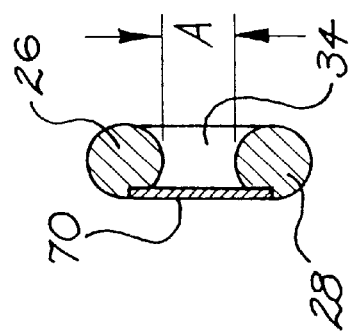

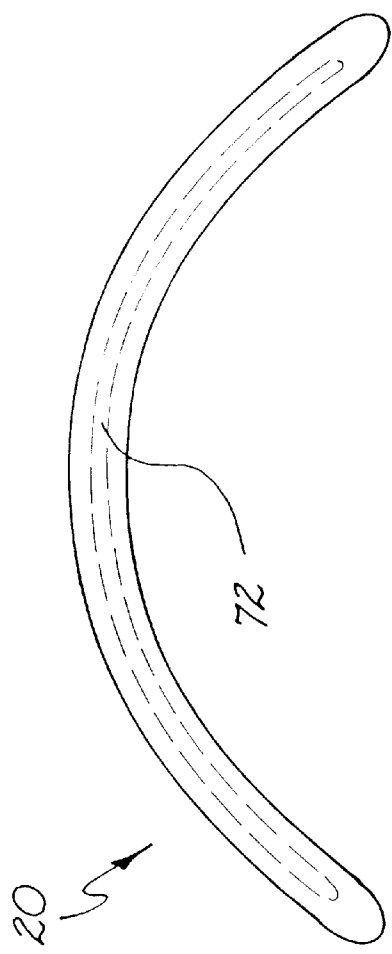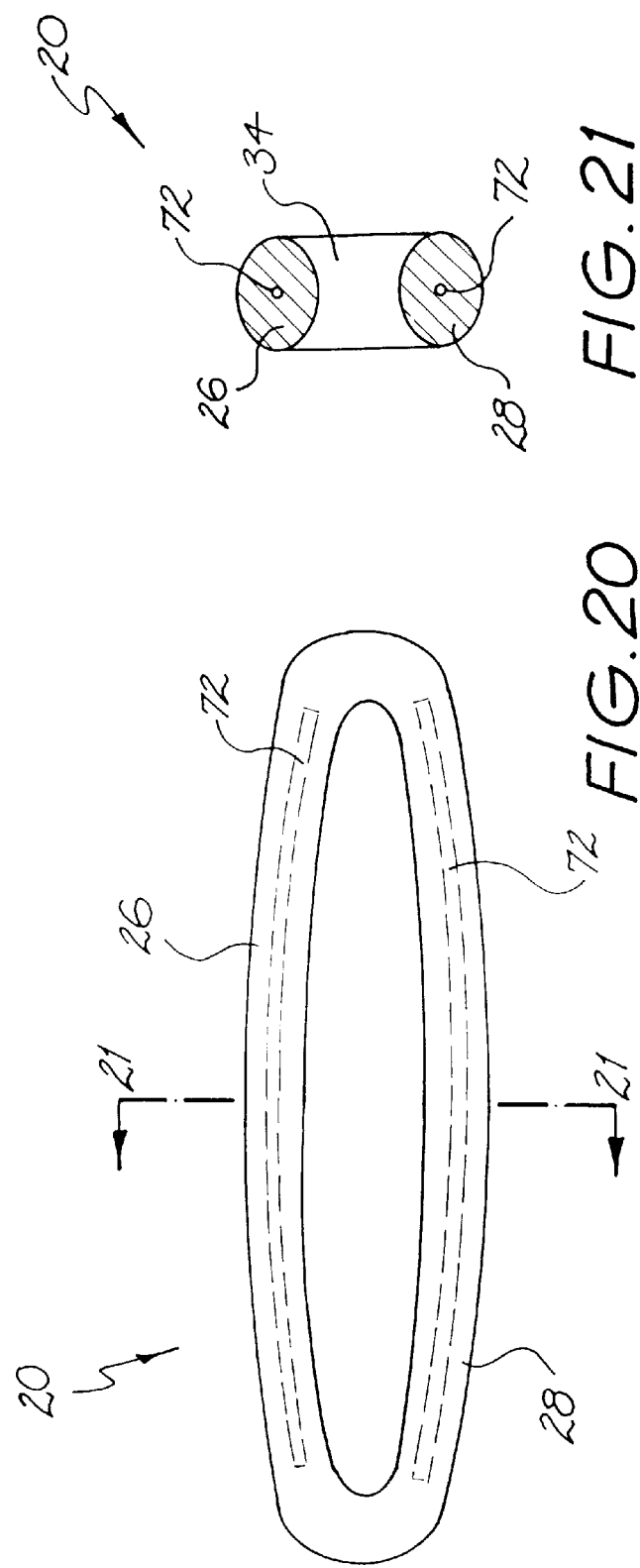

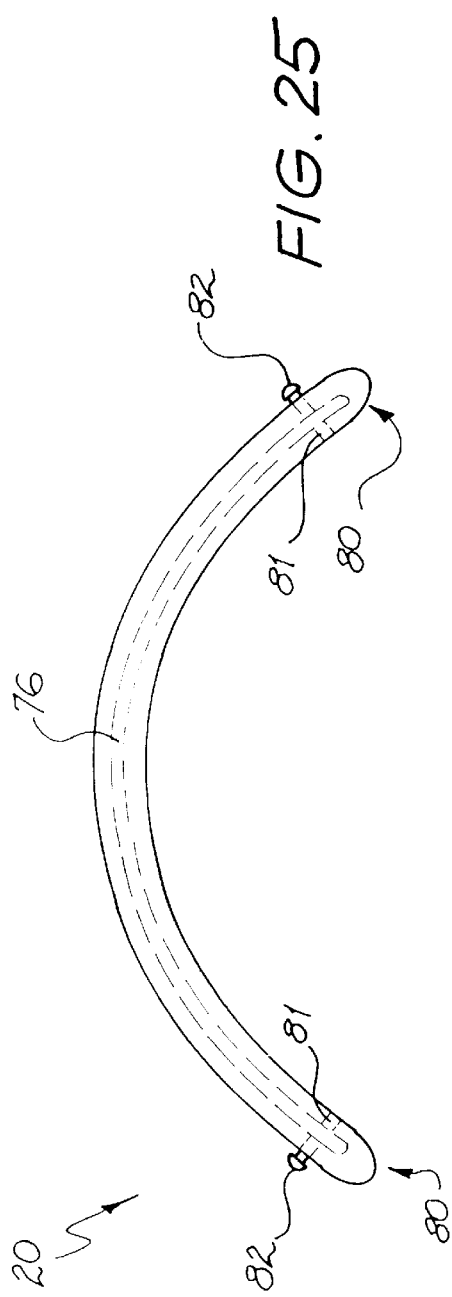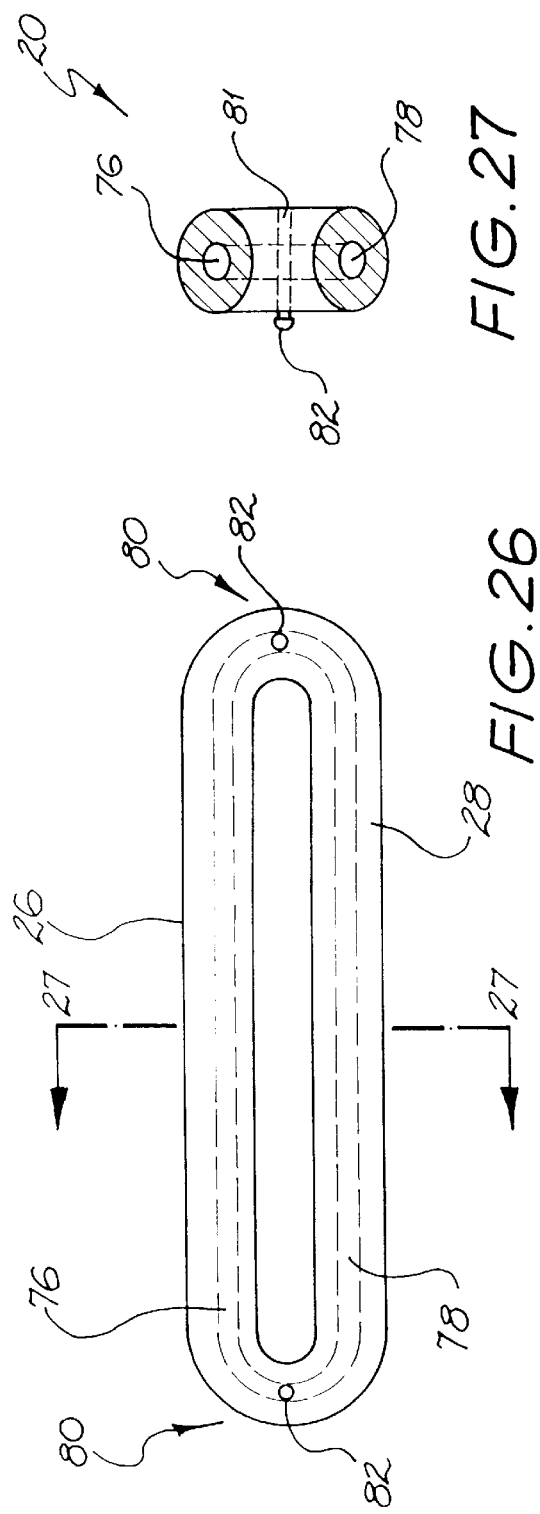

DEVICE FOR PREVENTING OR REDUCING THE PASSAGE OF AIR THROUGH THE MOUTH

FIELD OF THE INVENTION

The present invention relates to a device and method for preventing or reducing the passage of air through the mount. The invention has particular application in the fields of non-invasive nasal mechanical ventilation and nasal CPAP (continuous positive airway pressure) treatment.

BACKGROUND OF THE INVENTION

During non-invasive nasal mechanical ventilation, air or other breathable gas is supplied to a patient through a nose mask. The pressure of the supplied gas is varied during the breathing cycle. A pressure of around 4 to 20 cm $H_2O$ above atmospheric is generally used during expiration to splint open the upper airway and to improve gas exchange within the lungs. During inspiration, a pressure of around 0 to 40 cm $H_2O$ above the expiratory pressure is used to assist or replace the patient's own ventilatory efforts. Nasal CPAP, for example, for the treatment of obstructive sleep apnea, generally uses equal inspiratory and expiratory pressures.

A problem experienced by patients undergoing non invasive nasal mechanical ventilation or nasal CPAP treatment is that of air escaping (leaking) via the mouth. This leads to drying and dehydration of the nasal passages, reduction in the pressure of the treatment gas being delivered to the lungs, reduction in the amount of ventilatory assistance, and, where applicable, incorrect triggering ox cycling of ventilatory assistance devices.

Hitherto, there have been several approaches to attempt to solve this problem. One such approach has been the use of a chin strap to hold the jaw of the patient in a closed position. However, air has still been able to leak through the lips and in extreme cases the air cause the lips to flap in a "raspberry" fashion.

A variation of this approach involved adding a thick layer of cloth over the lips of the patient. Any air passing through the patient's lips must be forced through the cloth thereby reducing leakage. The device is uncomfortable and still allows air to leak through the patient's mouth.

Another approach has been to use a resilient mask shaped to the contours of the "average" patient's face. The mask is held in position by a head strap. To deform the mask material to form a fluid tight seal, and to account for variations from the average face, the strap often has to be tightened to an uncomfortable degree which may lead to non-compliance. FIGS. 1 and 2 show a mask 10 of this type being held in place by a strap 12. The mask 10 seals against the face 14 of the patient around the mouth, and the head strap 12 forces the mask 10 against the face 14 in the direction of arrows 16 to press and thereby seal the mask 10 against the face 14.

A variation of the above arrangement involves replacing the resilient mask with a bubble or balloon-like membrane that is inflated by the gas being supplied to the patient. This mask conforms to the contours of the face more readily and thus allows the strap forces to be reduced.

It is an object of the present invention to provide an improved device and/or method for preventing or reducing the passage of air through the mouth, and in particular to provide such a device and method where the force of the head strap may be substantially lessened or even obviated.

SUMMARY OF THE INVENTION

Accordingly, in a first aspect, the invention provides a device for preventing or reducing the passage of air through the mouth, the device comprising a top lip member and a bottom lip member having a space therebetween, whereby said space is configured such that, in use, when the top and bottom lips of a wearer are forced through the space they are squeezed against the top and bottom lip members respectively to thereby substantially seal the mouth.

In an embodiment, the device is preferably resilient and squeezes the lips together in a supero-inferior direction to substantially seal the mouth.

In another embodiment, the device is preferably formed from a relatively stiff material and the gas pressure in the mouth behind the lips forces them against the respective lip members and against each other to substantially seal the mouth.

Preferably, the top and bottom lip members engage or grip the top and bottom lips respectively when the device is in use.

In an embodiment, the top and bottom lip members are joined at at least one end. In another embodiment, the top and bottom lip members are joined at both ends thereby defining an aperture through which the lips are forced in use.

The device is desirably shaped to conform to the shape of the lips. When viewed from above, the device is curved or crescent shaped. When viewed from the front, the device is substantially oval.

The device can also desirably include a cover extending between the members. The cover provides a secondary seal for any air leaking past the lips. In a variation of this, the cover can include a vent to reduce the likelihood of pressure build up behind the cover in the event of minor or intermittent air leaks past the lips.

A preferred embodiment of the device includes a strap to assist in locating the device on the lips of the wearer.

In one form, the device is manufactured from a malleable material and is shaped to conform to the wearer's face. Alternatively or additionally, the device may include a malleable component embedded therein or attached thereto. In an embodiment, the malleable component can be a metal wire produced from, for example, aluminium, silver or steel.

In another form, the device is manufactured from a heat formable material and is heated, shaped to conform to the wearer's face and then allowed to cool and set. Alternatively or additionally, the device may include a heat formable component embedded therein or attached thereto. In an embodiment, the malleable component can be a plastics wire or ribbon.

The device is preferable manufactured from a silicone rubber, for example, Silastic 94-595-HC produced by Dow Corning Australia Pty Ltd.

BRIEF DESCRIPTION OF THE DRAWINGS

Preferred embodiments of the invention will now be described, by way of example only, with reference to the accompanying drawings in which:

FIG. 12 is a partial schematic side view of a device according to the third embodiment of the invention;

FIG. 13 is a plan view of the device shown in FIG. 12;

FIG. 14 is a front view of the device shown in FIG. 12;

FIG. 15 is a cross-sectional side view of the device shown in FIG. 12, along line 15—15 of FIG. 14;

FIG. 16 is a plan view of a device according to a fourth embodiment of the invention;

FIG. 17 is a front view of the device shown in FIG. 16;

FIG. 18 is a cross-sectional side view of the device shown in FIG. 16, along line 18—18 of FIG. 17;

FIG. 19 is a plan view of a device according to a fifth embodiment of the invention;

FIG. 20 is a front view of the device shown in FIG. 19;

FIG. 21 is a cross-sectional side view of the device shown in FIG. 19, along line 21—21 of FIG. 19;

FIG. 25 is a plan view of a device according to a seventh embodiment of the invention;

FIG. 26 is a front view of the device shown in FIG. 25; and

FIG. 27 is a cross-sectional side view of the device shown in FIG. 25, along line 27—27 of FIG. 25.

DESCRIPTION OF THE PREFERRED EMBODIMENTS

Referring to FIGS. 3 to 7, there is shown a first embodiment of a device 20 for preventing or reducing the passage of air through the mouth 22 of a wearer's head 24.

Figure 2:
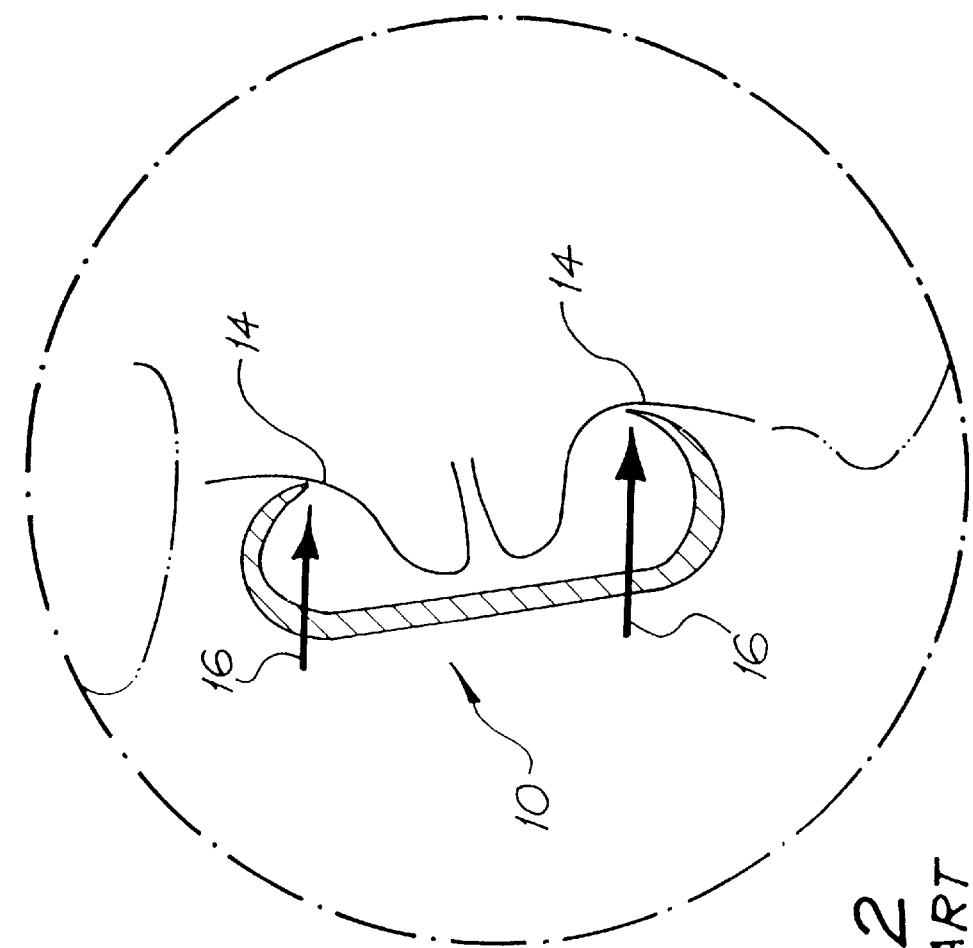
FIG. 2 is a partial enlarged view of the device shown in FIG. 1.
Figure 1:
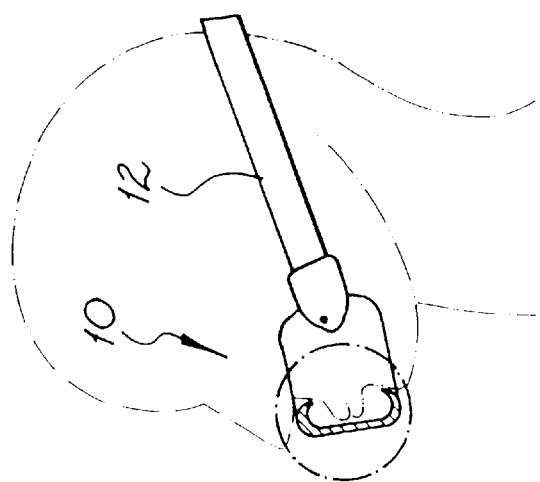
FIG. 1 is a schematic side view of a prior art device.
Figure 4:
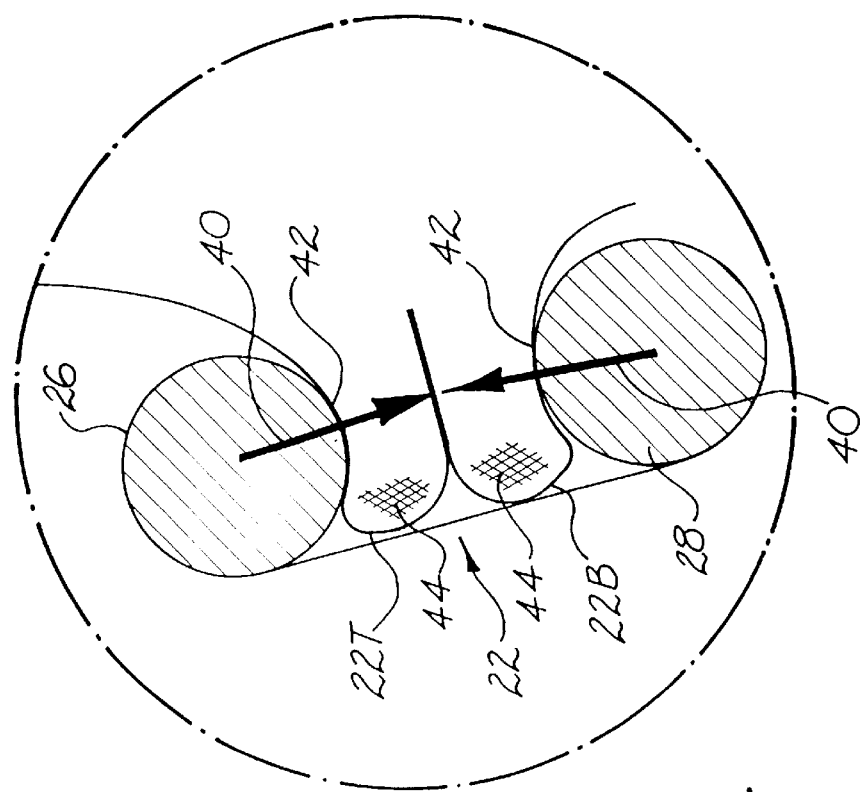
FIG. 4 is a partial enlarged view of the device shown in FIG. 3.
Figure 3:
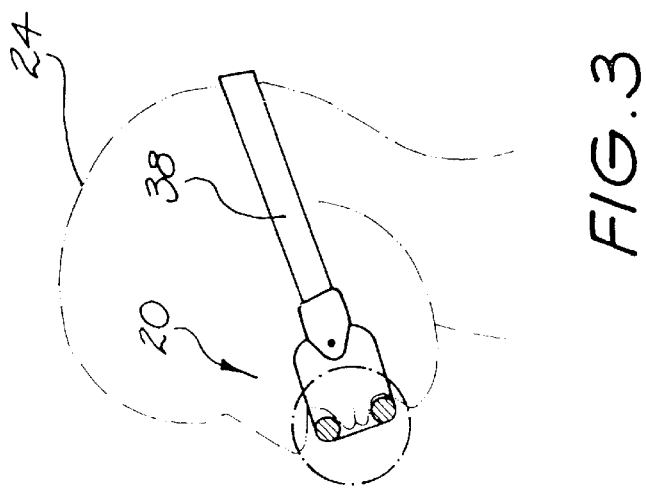
FIG. 3 is a schematic cross-sectional side view of a device according to a first embodiment of the invention.
Figure 5:
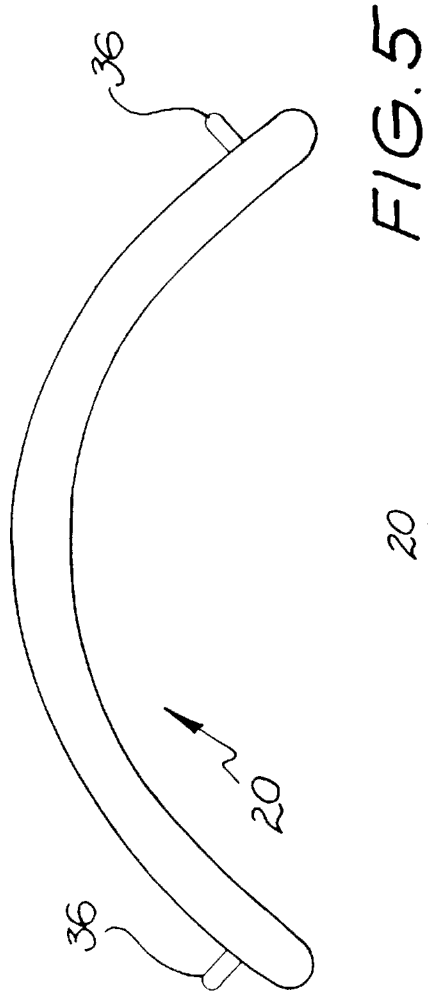
FIG. 5 is a plan view of the device shown in FIG. 3.
Figure 6:
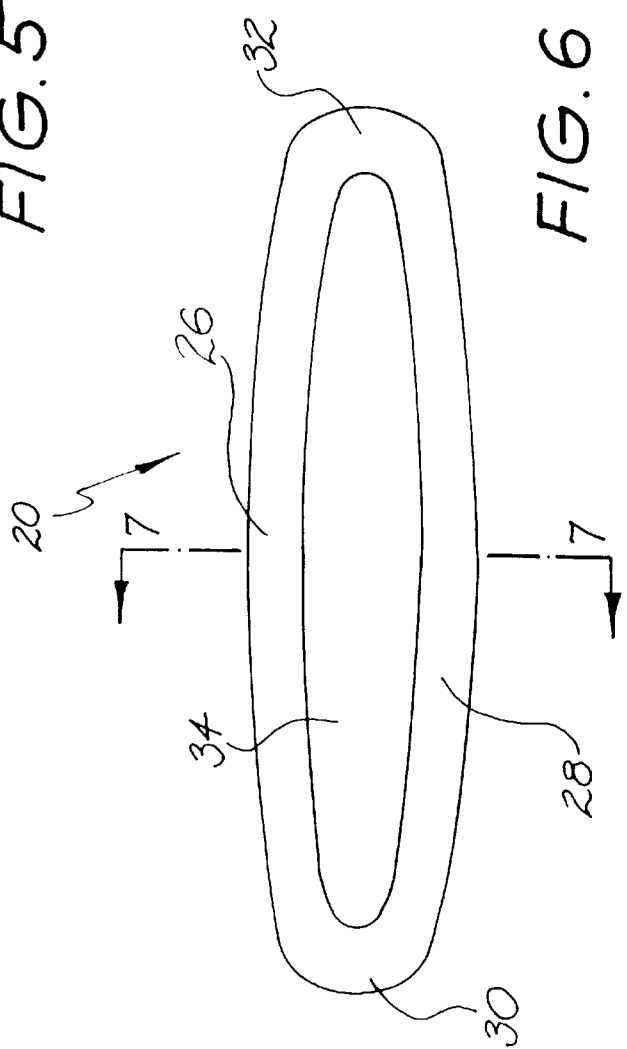
FIG. 6 is a front view of the device shown in FIG. 3.

The mouth includes a top lip 22T and a bottom lip 22B. The device 20 includes a top lip member 26 and a bottom lip member 28 which are formed from a resilient material. The resilient material can be, for example, a plastics material or a metal coated by a plastics material. As best shown in FIG. 6, the members are joined at ends 30 and 32 to define a space or aperture 34 therebetween.

When viewed from above (see FIG. 5) the device is curved in the general shape of the lips 22T and 22B. Hooks 36 are also provided adjacent the ends 30 and 32 of the device 20 to allow it to be attached to a strap 38.

To install the device 20, the lips 22T and 22B are pursed together and squeezed through the aperture 34. When the lips have been squeezed through the aperture 34 in this way the resilient top and bottom lips members 26 and 28 apply a compressive force to the lips 22T and 22B respectively, as indicated by arrows 40, to squeeze the lips together and thereby substantially seal the mouth.

The region 42 adjacent where the top and bottom lip members 26 and 28 abut the lips 22T and 22B are compressed slightly and the regions 44 that are forced through the device expand to a slightly bulbous configuration as shown. This bulbous configuration assists in retaining the device 20 in place.

The strap 38 is also used to retain the device in place and particularly to ensure the device is not dislodged during movement whilst the wearer is asleep. However, it is important to note that the strap does not necessarily have to apply a sealing force against the face or mouth.

The upper and lower lips 22T and 22B are squeezed together in the direction indicated by arrows 40 in the supero-inferior (top-to-bottom) direction. This causes frictional forces to arise between the lips themselves and also between each lip and its respective lip member which primarily retains the device in place.

Figure 7:
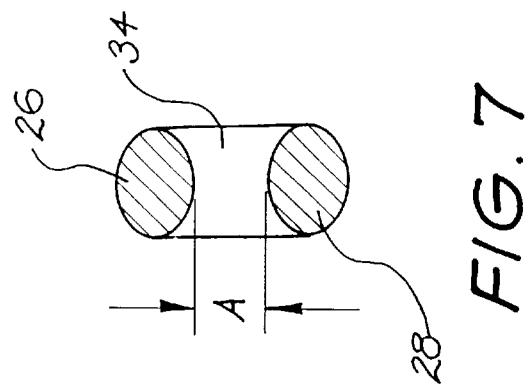
FIG. 7 is a cross-sectional side view of the device shown in FIG. 3, along line 7—7 of FIG. 6.
Figure 8:
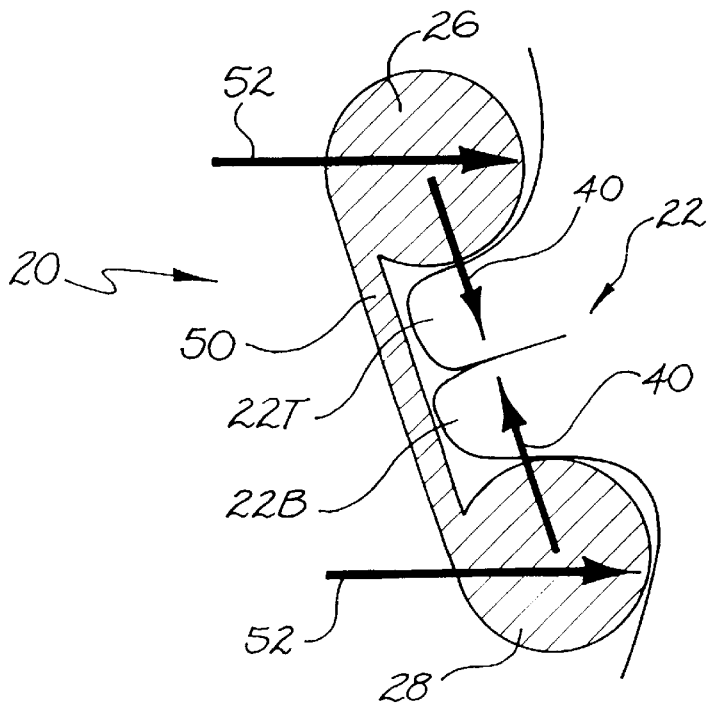
FIG. 8 is a partial schematic side view of a device according to the second embodiment of the invention.
Figure 9:
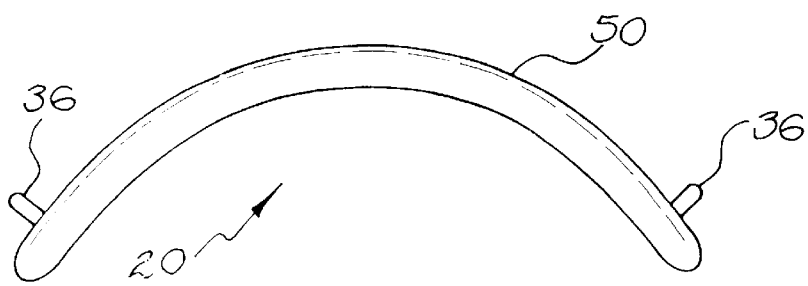
FIG. 9 is a plan view of the device shown in FIG. 8.
Figure 10:
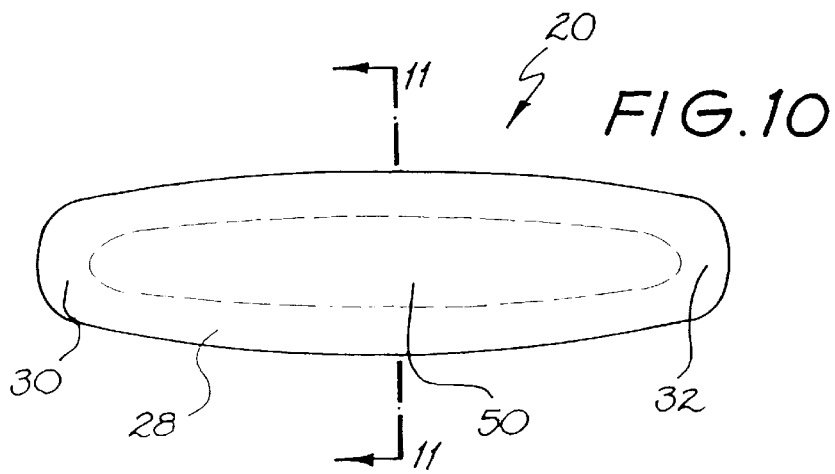
FIG. 10 is a front view of the device shown in FIG. 8.
Figure 11:
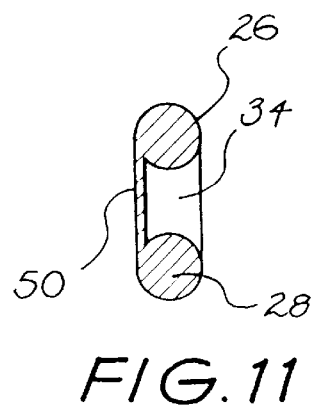
FIG. 11 is a cross-sectional side view of the device shown in FIG. 8, along line 11—11 of FIG. 10.
Figure 24:
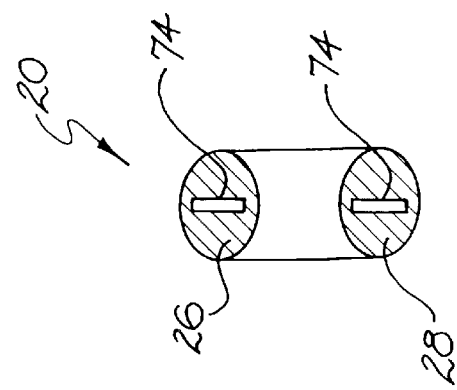
FIG. 24 is a cross-sectional side view of the device shown in FIG. 22, along line 24—24 of FIG. 22.
Figure 22:
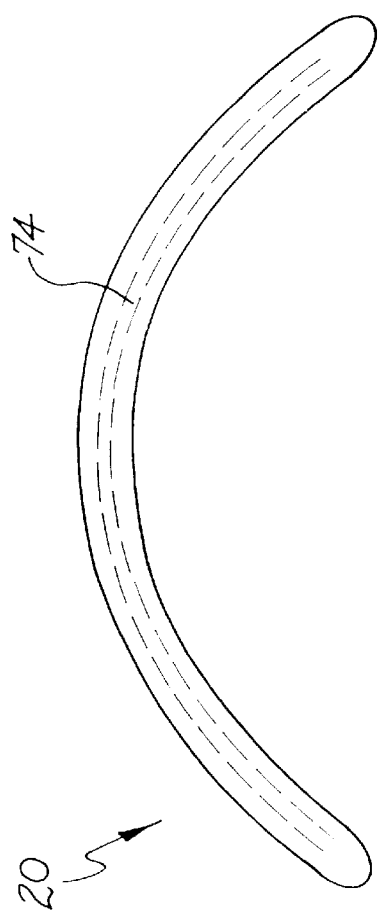
FIG. 22 is a plan view of a device according to a sixth embodiment of the invention.
Figure 23:
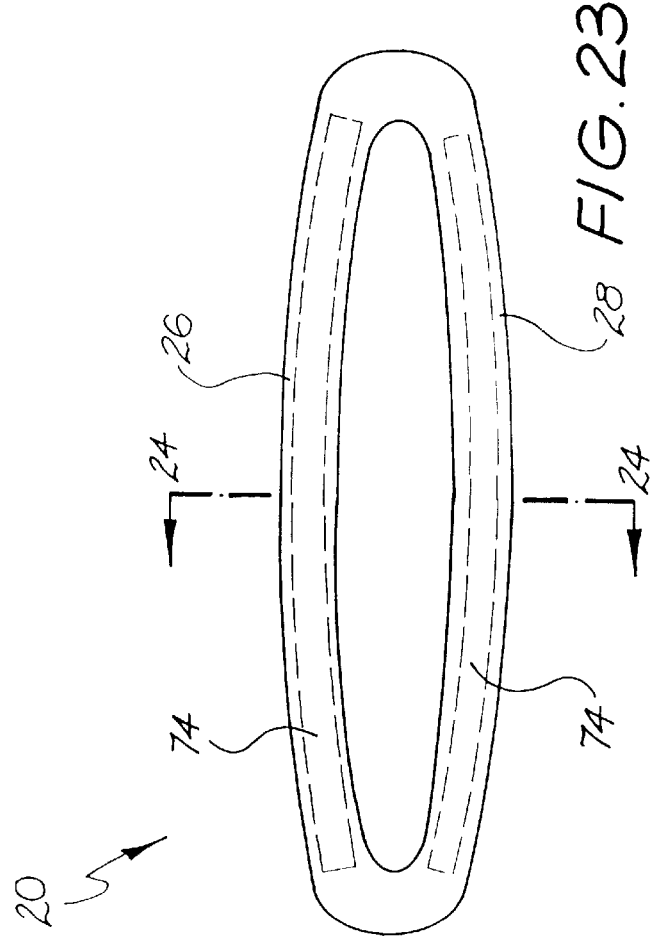
FIG. 23 is a front view of the device shown in FIG. 22.

Referring to FIG. 7, the width A of the aperture 34 is determined so as to compress the lips 22T and 22B together in a sealing manner without discomfort. The width of the device 20 is determined such that the ends 30 and 32 of the device 20 lie against the skin 10 or 20 mm to the left and right sides of the mouth 20 in the postero-lateral direction.

FIGS. 8 to 11 show a second embodiment of the invention in which like reference numerals will be used to indicate like features. This second embodiment includes a cover 50 sealing the outermost edge of the aperture between the top and bottom lip members 26 and 28. Thus, in this embodiment, any leakage of air past the lips that does occur is prevented from escaping to atmosphere by the seal 50. It should be noted that the primary sealing of the device 20 is due to the compressive force of the lip members 26 and 28 indicated by arrows 40. The forces in the direction of arrows 52 produced by the head strap generally only serve to retain the device in place. However, if necessary, the supero-inferior seal of the device according to the invention can be supplemented by the antero-posterior seal provided by the regions 54 of the top and bottom lip members 26 and 28 abutting the face adjacent the mouth 22 by tightening the strap 38, in which case the forces in the direction of the arrows 52 become larger to provide the antero-posterior seal.

FIGS. 12 to 15 show a third embodiment of the invention in which like reference numerals will be used to indicate like features. This third embodiment is a variation of the second embodiment and includes a high impedance vent 60 in the seal so that any small leaks past the supero-inferior seal of the lips do not cause a pressure build up behind the seal which might otherwise tend to dislodge the device 20. Also, in the event of a more severe failure of the supero-inferior seal, the antero-posterior seal, if utilized by tightening the straps, will provide an additional barrier to leak so that the leak is controlled to at most that which can pass through the vent 60.

FIGS. 16 to 18 show a fourth embodiment of the invention. Like reference numerals will again be used to indicate like features. In this embodiment, the device 20 includes a ribbon-like component 70 attached thereto. The component 70 is resilient and is bent or formed so as to be concave when viewed from the wearer To more closely comform the device 20 to the wearer's face. Metals such as aluminium, silver or steel are suitable for producing a resilient malleable component 70. Plastics are best suited for producing a resilient hear formable component 70.

The component 70 also allows the width A of the aperture 34 between the top and bottom lip members 26 and 28 to be set at a predetermined fixed distance so as to provide a consistent lip sealing force. The component 70 can also include a vent 60 as described in relation to the third embodiment.

FIGS. 19 to 21 and 22 to 24 show fifth and sixth embodiments of the present invention respectively which are similar to the first embodiment. In these embodiments, malleable or heat formable components 72 and 74 are moulded within the top and bottom lip members 26 and 28.

In the fifth embodiment, the components 72 are of circular cross section and in the sixth embodiment the components 74 are of flat ribbon-like cross section. The components 72 and 74 can be produced from the materials described in relation to the component 70 of the fourth embodiment.

FIGS. 25 to 27 show a seventh embodiment of the present invention. In this embodiment, the device 20 includes two substantially rigid steel wires 76 and 78 of 2 mm diameter embedded in the top and bottom lip members 26 and 28 respectively. The wires 76 and 78 are brass soldered together at ends 80 to join them together and form a loop. Two brass members 81 having external mushroom-shaped heads 82 are also soldered to the ends 80 to allow connection of the device 20 to a head strap (not shown) to assist in retaining the device 20 adjacent the lips of the wearer. The device 20 is positioned against the wearer's lip 22T and 22B by the neck strap which applies a small force to locate the device only. The gas pressure in the wearer's mouth 22 squeezes the lips 22T and 22B against the top and bottom lip members 26 and 28 respectively and against themselves to substantially seal the mouth.

The seventh embodiment can be produced by suspending the assembled loop of the wires 76 and 78 and the members 81 within an aluminium mould and then injecting the mould under pressure with liquid silicone rubber, such as the Silastic 94-595-HC previously described. The mould is then baked for about an hour at 180 degrees Celsius to cure the rubber. The other embodiments can be produced in a similar manner.

The seal between the lips and the device can be improved by providing extra grip between the lips and the contact surface of the lip members for example by making or coating the lip members with a material having a high co-efficient of friction or a non-toxic releasable adhesive, or by providing longitudinal grooves in the contact surfaces of the top and bottom lip members 26 and 28.

All of the above embodiments are preferably manufactured from Silastic 94-595-HC produced by Dow Corning Australia Pty Ltd.

INDUSTRIAL APPLICABILITY

The device according to the present invention provides advantages over those of the prior art. In particular, as the lips are sealed against each other by the supero-inferior compressive force, and because the compressive force producing the seal is supplied by the device gripping the lips, the device does not require a high force on the head strap to retain the device in place, thereby increasing the comfort of the wearer. Secondly, small movements of the head which may result in a temporary loosening or tightening of the head strap do not adversely effect the seal of the device compared to prior art devices. Thirdly, as the device tends to grip the lips and does not rely on a head strap it is less likely to be dislodged.

Moreover, the present invention provides a high degree of safety because a negligible restraining force is required to produce a seal. As a result, the wearer may easily break the seal to talk, cough or breathe through the mouth should the need arise. This is especially advantageous should the wearer's nasal airways become blocked or if the device delivering the gas supply to the wearer malfunctions.

Although the invention has been described with reference to specific examples, it would be understood by those skilled in the art that the invention is not limited to these particular examples and may be embodied in many other forms.

The claims defining the invention are as follows:

1. A device for reducing the passage of air through the mouth, the device comprising a top lip member and a bottom lip member having a space therebetween, whereby said space is configured such that, in use, when the top and bottom lips of a wearer are forced through the space, the top and bottom lips of the wearer are squeezed against the top and bottom lip members respectively to thereby substantially seal the mouth.

2. The device as claimed in claim 1, wherein the device is a resilient material.

3. The device of claim 2, wherein said top and bottom lip members squeeze the lips together in a supero-inferior direction.

4. The device as claimed in claim 1, wherein the device is formed from a stiff material.

5. The device of claim 4, wherein the gas pressure in the mouth forces the lips against the respective lip members and against themselves.

6. The device as claimed in claim 1, wherein the top and bottom lip members engage the top and bottom lips respectively when the device is in use.

7. The device as claimed in claim 1, wherein the top and bottom lip members are joined at at least one end.

8. The device as claimed in claim 1, wherein the top and bottom lip members are joined at both ends thereby defining an aperture through which the lips are forced in use.

9. The device as claimed in claim 1, wherein the device is shaped to conform to the shape of the lips.

10. The device as claimed in claim 9, wherein when the device is worn by a wearer whose head is in an upright position and, when viewed from above, the device is substantially crescent shaped.

11. The device as claimed in claim 10, wherein when the device is worn by a wearer whose head is in an upright position and, when viewed from the front, the device is substantially oval.

12. The device as claimed in claim 1, wherein the top and bottom lip members each comprise heat formable components.

13. The device as in claim 12, wherein the components comprise plastic materials.

14. The device as claimed in claim 12, wherein the components are joined at their adjacent ends to form a loop.

15. The device as claimed in claim 14, wherein the components have a substantially circular cross section.

16. The device as claimed in claim 14, wherein the components have a flat ribbon-like cross section.

17. The device as claimed in claim 16, wherein the components comprise metal.

18. The device as claimed in claim 17, wherein the metal is selected from the group consisting of aluminum, silver or steel.

19. The device as claimed in claim 1, wherein the device includes a cover extending between the top and bottom lip members.

20. The device as claimed in claim 19, wherein the cover comprises a heat formable material.

21. The device as in claim 20, wherein the cover is produced from plastic materials.

22. The device as claimed in claim 19, wherein the cover comprises metal.

23. The device as claimed in claim 22, wherein the metal is selected from the group consisting of aluminum, silver or steel.

24. The device as claimed in claim 19, wherein the cover includes a vent.

25. The device as claimed in claim 1, wherein the device includes a head strap attached to the ends of the device.

26. The device as claimed in claim 25, wherein the device includes external projections at each end thereof to facilitate attachment of the strap.

27. The device as claimed in claim 1, wherein the lip members are coated with a non-toxic releasable adhesive.

28. The device as claimed in claim 1, wherein the lip members comprise silicone rubber.

29. The device as claimed in claim 28, wherein the lip members comprise Silastic 94-595-HC produced by Dow Corning Australia Pty Ltd.

* * * * *